United States Patent [19]

Brian, III et al.

[11] Patent Number: 5,648,070

[45] Date of Patent: *Jul. 15, 1997

[54] BIOCOMPATIBLE ANION EXCHANGE MATERIALS

[75] Inventors: Ben F. Brian, III, Golden; Marc Voorhees, Arvada; Lloyd James Forrestal, Boulder, all of Colo.

[73] Assignee: Cobe Laboratories, Inc., Lakewood, Colo.

[*] Notice: The term of this patent shall not extend beyond the expiration date of Pat. No. 5,354,472.

[21] Appl. No.: 315,696

[22] Filed: Sep. 30, 1994

Related U.S. Application Data

[63] Continuation-in-part of Ser. No. 981,912, Nov. 23, 1992, Pat. No. 5,354,472, and a continuation of Ser. No. 802,185, Dec. 4, 1991, abandoned.

[51] Int. Cl.$^6$ ............................................. B01D 15/08
[52] U.S. Cl. ........................................ 424/78.1; 424/78.17
[58] Field of Search .................................. 424/78.1, 78.17

[56] References Cited

U.S. PATENT DOCUMENTS

| | | | |
|---|---|---|---|
| 3,472,840 | 10/1969 | Stone et al. | 260/231 |
| 4,048,064 | 9/1977 | Clark | 210/3 R |
| 4,070,287 | 1/1978 | Wiegand et al. | 210/40 |
| 4,355,117 | 10/1982 | Antrim et al. | 521/28 |
| 4,373,023 | 2/1983 | Langer | 435/2 |
| 4,663,163 | 5/1987 | Hou et al. | 424/101 |
| 4,678,468 | 7/1987 | Hiroyoshi | 623/1 |
| 4,678,660 | 7/1987 | McGary et al. | 424/25 |
| 4,690,973 | 9/1987 | Noishiki et al. | 525/54.1 |
| 4,800,016 | 1/1989 | Yang | 210/206 |
| 4,810,567 | 3/1989 | Calcaterra et al. | 428/224 |
| 4,936,998 | 6/1990 | Nishimura et al. | 210/638 |
| 5,151,192 | 9/1992 | Matkovich et al. | 210/646 |
| 5,354,472 | 10/1994 | Voorhees et al. | 210/635 |

FOREIGN PATENT DOCUMENTS

| | | |
|---|---|---|
| 0219053 | 4/1987 | European Pat. Off. |
| 0466178A1 | 1/1992 | European Pat. Off. |
| 035069 | 3/1979 | Japan |
| 2080056 | 3/1990 | Japan |
| 1601464 | 10/1981 | United Kingdom |

OTHER PUBLICATIONS

07/562,009 Aug. 2, 1989, Maddock.

Andrade et al., "Surfaces and Blood Compatibility" Trans. Am. Soc. Artif. Intern. Organs (1987) 33: 75–84.

Benerito, R.R. et al., "Preparation and Properties of Quaternary Cellulose Anion Exchanges," Anal. Chem. (1965) 37:1693–1699.

Brian, Ben F. III, Ph.D. Thesis (1991) entitled "Augmented Hemoperfusion for Hyperbilirubinemia".

Brian, Ben et al., Confidential disclosure of invention entitled "A Method for Producing Whole Blood Compatible Anion Exchange Materials" dated Feb. 12, 1991.

Cipoletti, J.J. et al., "Resin Technology in Medicine," Sorbents and Their Clinical Applications (Giordana ed.), Academic Press, New York, 1980, pp. 221–248.

Citovicky, P. et al., "Epoxy Groups on Grafted Polypropylene," Die Angewandte Makromolekulare Chemie (1989) 171:153–164.

(List continued on next page.)

Primary Examiner—Peter F. Kulkosky
Attorney, Agent, or Firm—Greenlee, Winner and Sullivan, P.C.

[57] ABSTRACT

Biocompatible anion exchange materials are provided comprising a support having a quaternary amine moiety and a polyethylene oxide (PEO) moiety having between about 10 and about 200 repeating units covalently bonded thereto, such that said quaternary amine and polyethylene oxide moieties are substantially homogeneously distributed on said support. These anion exchange materials are useful for removing negatively charged species such as heparin from blood and other body fluids without significant removal of platelets. Methods of making and using these materials are also provided.

33 Claims, 2 Drawing Sheets

OTHER PUBLICATIONS

Han, D.K. et al., "Preparation and surface characterization of PEO–grafted and heparin–immobilized polyurethanes," J. Biomed. Mater. Res.: Applied Biomaterials, (1989) 23(A1):87–104.

Hou et al., "A Method for Extracorporeal Heparin Removal from Blood by Affinity Chromatography," Art. Organs (1990) 14(6):436–442.

Hou, L.C. and Mandaro, R.M., "Bioseparation by Ion Exchange Cartridge Chromatography," BioTechniques, 358–366.

"IDE Sought for Heparin Removal Device", BBI Newsletter (Mar. 1994) 17(3):56–57.

Ito, H. et al., "Formatin of Polyelectrolyte Complexes between Cellulose Derivatives and Their Blood Compatibility," J. App. Polymer Sci. (1986) 31:2491–2500.

Matsuda, K. et al., "Experimental Study on the Adsorption of Excess Heparin with Anion Exchange Resin Fiber," Art. Organs (1989) 13(6):504–507.

Mori, Y. et al., "A New Antithrombogenic Material with Long Polyethyleneoxide Chains," Trans Am. Soc. Artif. Intern. Organs (1982) 28:459–463.

Shechter, L. and Wynstra, J., "Glycidyl Ether Reactions with Alcohols, Phenols, Carboxylic Acids, and Acid Anhydrides," Industrial and Engineering Chemistry, (1956) 48(1):86–93.

Shechter, L. et al., "Glycidyl Ether Reactions with Amines," Industrial and Engineering Chemistry, (1956) 48(1):94–97.

Sideman, S. et al., "Resin Hemoperfusion for Unconjugated Bilirubin Removal," Contr. Nephrol. (Karger, Basel 1982) 29:90–100.

Soignet, D.M. et al., "Comparison of Properties of Anion–Exchange Cottons in Fabric Form", Textile Res. J. (1966) 978–989.

Tanaka, H. and Ödberg, L., "Preparation of Cationic Polyacrylamides by a Modified Hofmann Reaction: Fluorescent Labeling of Cationic Polyacrylamides," J. Polymer Sci: Part A: Polymer Chemistry (1989) 27:4329–4339.

Wilson, "How Surface–Bound Drugs Inhibit Thrombus Formation,", Drug. Dev. Res. (1990) 21:39–92.

∇ PROTAMINE (n = 1)
□ COBE-HRF (n = 3)
○ CUNO-QAE (n = 3)

▽ CONTROL (POLYESTER)
□ COBE-HRF (n = 3)
◊ UNTREATED SUBSTRATE
○ CUNO-QAE (n = 3)

BIOCOMPATIBLE ANION EXCHANGE MATERIALS

CROSS-REFERENCE TO RELATED APPLICATIONS

This application is a continuation-in-part of U.S. Ser. No. 07/981,912, filed Nov. 23, 1992, now U.S. Pat. No. 5,354,472 and a continuation of U.S. Ser. No. 07/802,185, filed Dec. 4, 1991, now abandoned, both of which are incorporated herein by reference,

FIELD OF THE INVENTION

This invention describes novel biocompatible anion exchange materials and methods for their production and use. In addition, this invention discloses methods of treatment of biological fluids such as whole blood for the selective removal of anionic species such as heparin.

BACKGROUND OF THE INVENTION

There are a wide number of applications where it is desirable to remove anionic (negatively charged) species or chemicals from whole blood. For example, anionic exchange materials—supports that have cationic or positively charged surfaces—have been suggested for the removal of barbiturates in drug overdose cases, bilirubin from jaundiced patients and heparin for the prevention of post-operative bleeding. See, e.g., Cipoletti et al., Resin Technology in Medicine in *Sorbents and Their Clinical Applications*, Giordano ed., Academic Press, New York, 1980; Sideman et al., *Contr. Nephrol.* (1982) 29:90–100; U.S. Pat. No. 4,800,016 of Yang; Matsuda et al., *Art Organs* (1989) 13:504–7; Hou et al., *Art Organs*, (1990) 74:436–442.

Supported cationic surfaces have also been suggested for the removal of coagulation factors at polymer surfaces for reduced thrombogenicity and improved biocompatibility. See, Wilson, *Drug Dev. Res.*, (1990) 21:79–92.

Despite the promise of such techniques, the use of anionic exchange materials in whole blood applications has been limited by the biocompatibility of the materials used. With the materials used to date, all researchers have noticed a demonstrable removal of platelets—and to a lesser extent white blood cells—from the whole blood samples passed over anion exchange supports. Previous attempts have been made to coat or shield the cation on the surface of the support materials in order to prevent the removal of blood components while retaining the ability to associate with anionic species in the whole blood sample. Such attempts have led to reductions in efficiency and/or capacity to remove anionic species from the whole blood. This is especially true where the anionic species that are being removed from the blood are relatively large (heparin, coagulation factors, etc.).

U.S. patent application Ser. No. 07/562,009, now U.S. Pat. No. 5,474,772 is commonly assigned with the present application. In the '009 Application, a method of medical treatment is described wherein a medical agent is administered to a patient and, after a period of time, the medical agent is removed extracorporeally by passing body fluid over a support adopted to immobilize the agent. Several embodiments of the present invention are adaptable for use in the method described in the '009 Application due to the biocompatibility of the anion exchange materials disclosed herein.

In one such embodiment, and in variations thereof, it is desirable to remove heparin from whole blood. Extracorporeal circulation of blood—required in many surgical and medical procedures—requires the use of systemic heparin to prevent coagulation. Heparin is a highly negatively charged compound. In almost all cases it is necessary to neutralize or remove the heparin in the patient's blood prior to the completion of the surgical procedure. This is required to prevent post-operative bleeding complications. The most commonly used means for neutralizing heparin in this situation is by treatment with protamine sulfate. Unfortunately, the administration of protamine sulfate has several adverse side effects.

Other efforts to remove heparin from whole blood have been investigated. For example, U.S. Pat. No. 4,373,023 of Langer describes a support on which heparinase, an enzyme that degrades heparin, has been immobilized. Others have attempted to use supported or immobilized protamine for heparin removal. See U.S. Pat. No. 4,800,016 of Yang; and Hou et al., *Art Organs*, (1990) 14:436–442.

Affinity or ion exchange chromatography allows purification or separation of most chemicals based on the molecule's biological function or chemical structure. The separation process occurs because of variations in affinity between the individual members of a mixture of components to a ligand or reactive group which is immobilized on an insoluble support or substrate. The substrates used in affinity chromatography generally are openly porous, have large surface areas, and contain some functionality that can be easily modified for the introduction of ligands. See, for example, Dean & Johnson, *Affinity Chromatography: a Practical Approach*, IRL Press, Oxford, 1985. The support materials preferably are strong, relatively heat-insensitive, and do not grow or "swell" significantly when in solution.

A common substrate or support is agarose beads, which possess a high degree of surface hydroxyl groups (—OH). The hydroxyl group is ideal for support materials due to its ability to be easily converted to other reactive functionalities such as aldehydes, or to be directly reacted with desired ligands. Ion exchange materials configured as flat, flexible sheets have found widespread use as support materials due to their physical characteristics and ease of use. See, for example, U.S. Pat. No. 4,663,163 of Hou. The sheet supports are commercially available with a variety of reactive groups such as hydroxyl, amine or aldehyde functionalities.

Efforts to make affinity or chromatographic materials biocompatible have been made in the past. Akizawa, T. et al. (1989), Abstracts ASAIO, discloses the use of a cellulose membrane having polyethylene glycol grafted thereon to suppress blood membrane surface interactions. The use of polyethylene oxide moieties on the surface of the materials to increase biocompatibility to surfaces for certain purposes has been described. See, U.S. Pat. Nos. 4,424,311 of Nagaoka et al.; 4,678,468 of Hiroyoshi; and Han, D. K. et al., "Preparation and surface characterization of PEO-grafted and heparin-immobilized polyurethenes," J. Biomed. Meths. Res. (1989) 23:87–104. It has been shown that the ability to confer biocompatibility is proportional to the chain length of the polymer units attached to the surface of the support. See, e.g., Mori et al., *Trans Am. Soc. Artif. Intern. Organs*, (1982) 28:459–463; Andvade et al., *Trans Am. Soc. Artif. Intern. Organs*, (1987) 33:75–84.

In a further reference, a heparin/hydrogel coating was described as a method of improving the biocompatibility of activated carbon for hemoperfusion. See, U.S. Pat. No. 4,048,064 of Clark. Macroreticular resin material or coated activated charcoal may also be used in the disclosed process and produce biocompatible hemoperfusion materials.

Other researchers have used quaternary ammonium chemicals to ionically bind an antithrombic agent to a surface. In U.S. Pat. No. 4,678,660 of McGary et al., heparin was complexed with the quaternary compound tridodecyl methyl ammonium chloride and incorporated into polyurethane. In U.S. Pat. No. 4,690,973 of Noishiki et al., glycidyl trimethyl ammoniumchloride (GTMAC) was reacted with collagen, and heparin was immobilized on the surface.

Despite the desirability of obtaining biocompatible anion exchange materials, the prior art does not describe any attempt to include immobilized cationic species and polyethylene oxides in such a way as to obtain the materials disclosed herein. The positive charge required for removal of negatively charged materials such as heparin also removes blood components such as platelets. It was therefore surprising to find that an anion exchange material could be made which would remove heparin without removing significant amounts of platelets or other necessary blood components.

All publications and patents referred to herein are incorporated by reference in their entirety.

SUMMARY OF THE INVENTION

The ion exchange materials of the present invention are prepared by the simultaneous or serial treatment of a support material with chemicals that place both quaternary ammonium functionalities and polyethylene oxide units on the surface of the support. The anion exchange materials as disclosed herein are capable of retaining their anion exchange capabilities while also being biocompatible with the components of whole blood. In a preferred embodiment, the anion ion exchange material is used to remove heparin from whole blood.

The present invention provides a biocompatible anion exchange material comprising a support having an anion exchange moiety and a biocompatibility moiety covalently bonded thereto. The anion exchange moiety is preferably an amine presenting a positively charged nitrogen, more preferably a tertiary or quaternary amine, and most preferably a quaternary amine. The support preferably should have a positive charge strong enough to ionically bond at least about 50 mg heparin per gram of support material as measured by equilibrium uptake using sheets of the support material having 150 cm$^2$ surface area per gram, soaked in heparin solution overnight. More preferably, the support materials of this invention are capable of absorbing up to about 250 mg heparin per gram. The biocompatibility moiety is a noncharged or weakly charged moiety having a chain length equivalent to about 10 to about 200 ethylene oxide units spaced closely enough on said support to prevent direct contact with said support by large molecular weight bodies such as platelets having a size greater than about 1 μm.

In a preferred embodiment, the biocompatible anion exchange material of this invention comprises:
 a. a support;
 b. a quaternary amine moiety covalently bonded to said support;
 c. a polyethylene oxide (PEO) moiety having between about 10 and about 200 repeating units covalently bonded to said support;
wherein said quaternary amine and said polyethylene oxide moieties are substantially homogeneously distributed on said support at a molar ratio of charged nitrogen on the quaternary amine to ethylene oxide repeating unit of between about 0.3:1 and about 450:1.

The term "biocompatible" as used herein means that the material does not substantially dissolve in blood or other body fluids, and does not significantly remove platelets, proteins other than target anions, or other blood or body fluid components having a negative charge. Blood and other body fluids which have been placed in contact with the anion exchange material of this invention may be introduced or re-introduced into the body without appreciable toxicity or depletion of fluid components.

The term "anion exchange material" is used in its art-known meaning to describe a material having a cationic surface capable of capturing or immobilizing anionic or negatively charged species such as heparin thereon when contacted with such species, typically by passing a solution of the negatively charged species over the surface.

A support material of this invention may be any support material known to the art which can provide immobilization for the cationic charge. The surface may be a solid or rigid surface such as provided by structural portions of a medical device, or may be flexible.

A quaternary amine moiety is covalently bonded to the support material by means of chemical reactions known to the art. For example, the support material may initially have reactive groups, such as hydroxyl, including glycol, epoxy, glycidyl, carbonyl, phenolic, aldehyde, carboxyl, cyanate, and/or amine, which may be reacted with similar reactive groups on the quaternary amine to form a covalent bond. Preferably the support material initially comprises reactive hydroxyl groups which react with epoxy, or glycidyl groups on the quaternary amine. After reacting with the quaternary amine and the PEO, the support should be insoluble in and relatively non-reactive with whole blood components other than the desired anionic species.

Suitable support materials can be made from polysaccharides including cellulose and agarose, polyurethanes, nylons, polyvinyl alcohol, polystyrenes, polyacrylamides and combinations thereof. Other materials known to the art such as polyolefins (such as polypropylenes) may be used or modified to present the necessary reactive groups for reacting with the quaternary amines. See, e.g., Citovicky, P. et al., "Epoxy Groups on Grafted Polypropylene," Die Angewandte Makro Molekulare Chemie (1989) 171:153–164, which discloses the modification of polypropylene to present epoxy reactive groups and the reaction thereof with amine-containing reactants such as dipropylamine, propylbenzylamine and other secondary amines, and Tanaka, H. and Odberg, L., "Preparation of Cationic Polyacrylamines by a Modified Hofmann Reaction: Fluorescent Labeling of Cationic Polyacrylamides," J. Polymer Science (1989) 27:4329–4339.

The quaternary amine is preferably one having methyl groups at the positions on the nitrogen adjacent to the position directly or indirectly bonded to the support material. A preferred quaternary amine for use in this invention is glycidyl trimethyl ammonium chloride. Other useful quaternary amines include epoxy propyl triethyl (or trimethyl) ammonium chloride, 2-hydroxylethyl trimethyl ammonium chloride (choline chloride), (2-aminoethyl) trimethyl ammonium chloride, and other quaternary amines having at least one reactive group such as hydroxyl, epoxy (e.g., glycidyl), aldehyde, carboxylic, carbonyl, phenol, cyanate and/or amine.

It should be understood that any species presenting a positively charged nitrogen in solution may be useful in this invention, e.g., diethyl aminoethyl or triethylamine. These amines can be quaternized by the addition of alkyl halides such as epichlorhydrin. Whether or not quaternized, such amines are included within the scope of this invention. Cellulose bearing secondary, tertiary and quaternary amines are described in Soignet, D. M. et al., "Comparison of Properties of Anion-Exchange Cottons in Fabric Form," Textile Res. J. (Nov. 1966) 978–989. These materials further modified as described herein, e.g., by reaction with bisamine polyethylene oxide, are biocompatible ion exchange materials of this invention. Benerito, R. R. et al., "Preparation and Properties of Quaternary Cellulose Anion Exchangers," Anal. Chem. (1965) 370:1693–1699, discusses diethylaminoethyl cellulose reacted with methyl iodide or methyl bromide to form a quaternary amine anion exchange material. Again, further reaction of this material with a bisamine polyethylene oxide as described herein results in biocompatible anion exchange materials of this invention.

The polyethylene oxide moiety of this invention preferably has between about 10 and about 200 repeating units, and also has a reactive group at one or both ends of the chain capable of covalently bonding with the reactive groups on the support material. Preferably the polyethylene oxide used to react with the support is bis glycidyl polyethylene oxide. The polyethylene oxide preferably has at least about 25 repeating units, and more preferably has between about 70 and about 80 repeating units.

The term "substantially homogeneously distributed" referring to the distribution of quaternary amine and polyethylene oxide on the support material means that these species occur at a substantially constant ratio to each other on any given area of the support. The support may contain areas of higher or lower concentration of both these species, but the ratio of each to the other should not substantially vary.

Preferably the ratio of quaternary amine to polyethylene oxide is one which allows substantial removal of negatively charged species of a molecular weight of up to about 45,000, preferably between about 6000 and about 30,000 daltons, while providing a sufficient amount of surrounding polyethylene oxide chains to block access to the cationic species by larger fluid components such as platelets, white blood cells, and red blood cells having sizes greater than about 1 μm. A preferred ratio of quaternary amine group to ethylene oxide repeating unit is between about 0.3:1 and about 450:1, more preferably between about 3:1 and about 50:1.

A process for preparing an anion exchange material is also provided herein comprising:

a. providing a support material comprising reactive groups capable as serving as covalent bonding sites;

b. contacting said support material with a quaternary amine and a polyethylene oxide having between about 10 and about 200 repeating units, said quaternary amine and said polyethylene oxide each having reactive groups capable of reacting with said reactive groups of said support material to form covalent bonds, whereby said quaternary amine and said polyethylene oxide are covalently bound to said support material.

Preferably the reaction is carried out in one step by contacting the support material with a solution having both the polyethylene oxide and the quaternary amine solubilized therein, such as an aqueous solution having a pH of between about 9 and about 13, adjusted preferably with sodium hydroxide. This one-step reaction is facilitated by having the reactive group on either the support or the quaternary amine and polyethylene oxide species be an epoxy group.

The solution and support material are kept in contact for a period of between about 0.5 and about 24 hours until the desired cationic charge has been imparted to the support surface.

This method produces biocompatible anion exchange materials suitable for efficient and effective removal of heparin from blood without significant platelet removal.

The support material may be incorporated into a blood processing apparatus, such as by forming solid surfaces of the apparatus with this support material, or by incorporating the material into filters and the like which may be contacted with blood or other bodily fluids containing heparin or other negatively charged species whose removal is desired. Preferably, the apparatus allows for the removal of heparin from the blood of a patient by contacting the heparinized blood with the biocompatible anion exchange material of this invention such that substantially all the heparin added to the patient's blood to prevent clotting during medical procedures is removed, leaving only that amount necessary to complete the surgical procedure, without significant removal of platelets, and then returning the processed blood to the patient.

"Significant" removal of platelets refers to removal of more than about 20 percent. The method for removing anionic materials from blood without significant removal of platelets provided herein preferably removes less than about 20 percent of platelets while removing the desired amount of said anionic material. As is understood in the art, physiologically effective amounts of heparin must remain in blood being returned to a patient's body to prevent clotting of the blood. Total removal of such other anionic species as barbiturates is desirable. Applicants have demonstrated removal of up to 99.8% of the anionic species heparin while removing only about 12% of platelets.

The blood or bodily fluid may be recirculated through the device as many times as necessary to remove the desired amount of anionic material. Generally, about 225 ml of heparinized blood (containing about 8 units/ml heparin) per 200 $cm^2$ of the anion exchange material of this invention can be treated allowing a contact time of not more than about 15 minutes.

This invention also comprises a method of treating a patient comprising:

a. removing blood from said patient;

b. adding heparin to said blood;

c. processing the heparinized blood;

d. removing heparin from the processed blood by passing it in contact with a biocompatible anion exchange material comprising a support having an anion exchange moiety and a biocompatibility moiety covalently bonded thereto; and e. returning the blood to the patient.

This invention also comprises a method of treating a patient comprising:

a. administering an anionic medical agent to a patient; and b. removing said medical agent from said patient by extracorporeally passing a bodily fluid of said patient in contact with a biocompatible anion exchange material comprising a support having an anion exchange moiety and a biocompatibility moiety covalently bonded thereto.

DETAILED DESCRIPTION OF THE PREFERRED EMBODIMENTS

Figure 1:
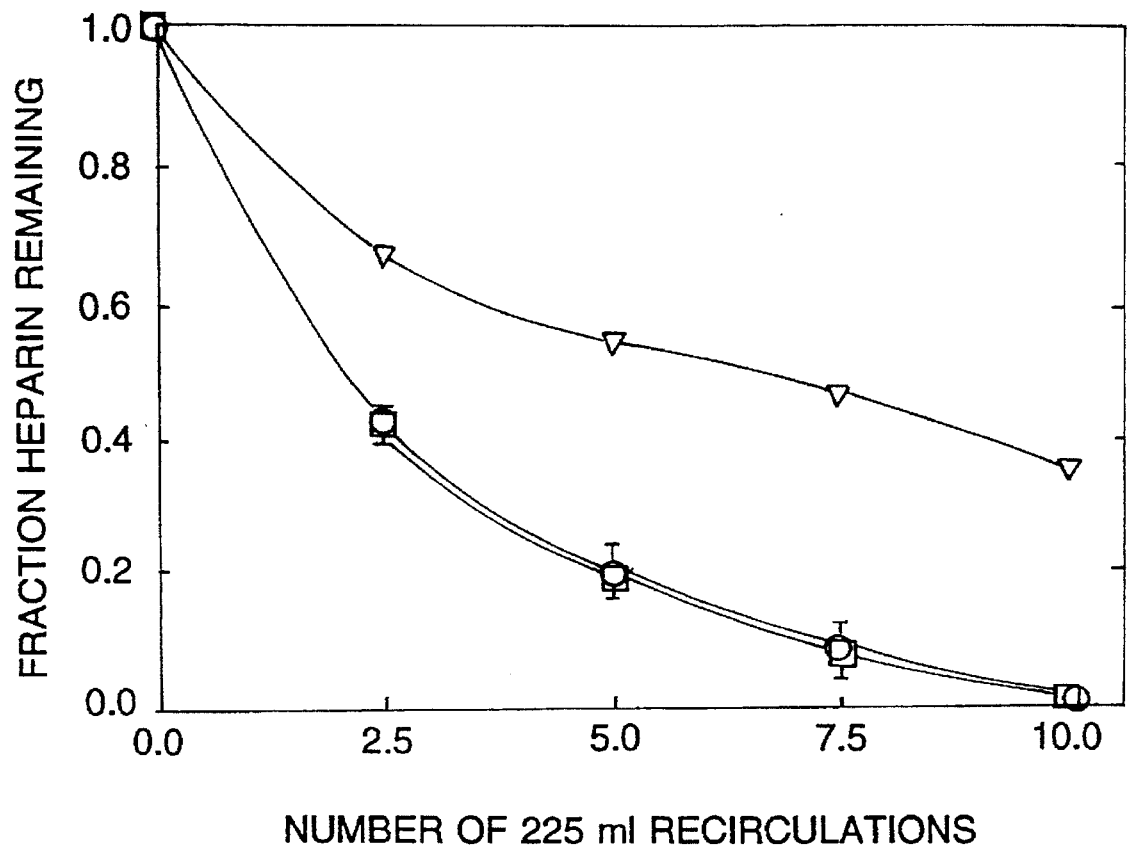
FIG. 1 is a graph that depicts the in vitro removal of heparin from bovine blood. The graph plots the fraction of heparin remaining in the blood sample versus the number of times the total volume of blood was circulated in contact with a given chromatographic material. Results are shown for a supported protamine (▽), a biocompatible anion exchange material of the present invention (□), and a commercially available anion exchange material known as Cuno QAE (○).

This invention describes novel biocompatible anion exchange materials. Anion exchange materials are used in a variety of purification or separation procedures. In some cases such materials can be used in batch reactions, but they are more typically used in flow or chromatographic procedures. Given compounds in a solution may be separated or purified based on the relative affinities of materials in a mixture to the reactive group on the surface of the anion exchange material. Anion exchange materials are a subspecies of a general class of affinity chromatographic materials.

The anion exchange materials of the present invention are comprised of a carrier support which has been treated with a plurality of reagents so that the surface of the support contains ion exchange elements and biocompatibility elements.

The carrier support may be comprised of any of the widely known and commercially available support materials commonly used by those skilled in the art. Carrier supports are typically highly porous, have a relatively large surface area, and have reactive functionalities. Detailed descriptions of the history of the development of carrier supports and the commonly used methods for converting carrier supports into affinity materials are described in U.S. Pat. No. 4,663,163 of Hou, and Dean, Johnson & Moddle (eds.), *Affinity Chromatography: A Practical Approach*, IRL Press, Oxford, 1986, both of which are incorporated herein by reference.

The biocompatible anion exchange material of this invention is prepared from a solid support material having reactive functional groups, preferably selected from the group consisting of hydroxyl, including glycol; epoxy; carboxyl; carbonyl; aldehyde; and amine. These reactive functional groups are reacted with quaternary amines having similar functional groups which are reactive with the reactive functional groups on the support material to form a covalent bond between the charged amine and the support material. The support material is also reactive with a polyethylene oxide having between about 10 and about 200 repeating units and also having a functional reactive group which will form a covalent bond with the reactive group on the support material.

Suitable supports include cellulose and agarose having reactive hydroxyl groups, polyurethane reacted with isocyanate to have reactive cyanate groups, amine-substituted nylon, or other base polymers which have been coated or reacted to provide hydroxyl, phenol, amino, carboxylic, cyanate, carbonyl aldehyde or epoxy reactive groups, or mixtures of the foregoing.

Reactive supports having stabilized amino, aldehyde, hydroxyl or carboxylic groups are available under the trade names Zetaffinity™ from Cuno, Inc., 400 Research Parkway, Meriden, Conn. 06450, or under the trade name Cellufine™ from Amicon Division, W. R. Grace & Co., 24 Cherry Hill Drive, Danvers, Me. 01923 and other sources known to those experienced in the art.

Preferably, either the support material or both the quaternary amine and polyethylene oxide utilize epoxy as the reactive group. The quaternary amine and polyethylene oxide are preferably the epoxy-containing groups. When epoxy is used as a reactive group to effect covalent bonding, the preparation of the anion exchange material can be carried out in one step involving solubilizing the quaternary amine and the polyethylene oxide in a single solution in aqueous solvents catalyzed by acid, base or tertiary amine, or in organic solvents including dioxane, heptane and methanol catalyzed by phenol, cresol, acid, base, or zinc tetra fluoroborate, and contacting the support material with the solution. In the preferred embodiment, aqueous solution pH should be adjusted to between about 9 and about 13 with any suitable reagent known to the art, preferably sodium hydroxide, prior to contact with the support material.

The biocompatible anion exchange material of this invention preferably contains the following structure:

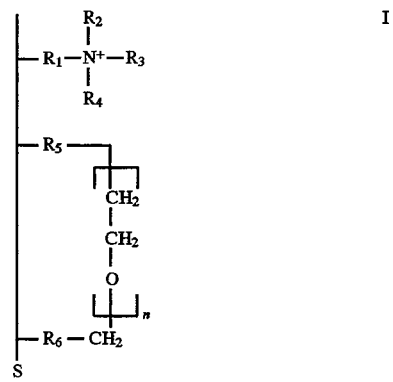

where S is a support material selected from the group consisting of polysaccharides including cellulose and agarose, or other polymers coated, modified or naturally containing reactive hydroxyl, amine, carboxylic, phenol, carbonyl, cyanate, aldehyde or epoxy groups.

$R_1$, $R_2$, $R_3$, $R_4$, $R_5$ and $R_6$ may be long or short chains, straight or branched, aliphatic or aromatic, and may be substituted with carboxyl, carbonyl, hydroxy, ether, ester or aldehyde. $R_1$ and $R_5$ and $R_6$ may contain these groups either from the support material or reactant(s), or as a result of their reactions. "n" is 10 to 200.

In a preferred embodiment, the quaternary amine compound, glycidyl trimethyl ammonium chloride, and the polyethylene oxide compound, bis glycidyl polyethylene oxide, both contain reactive epoxy groups which react with surface hydroxyl groups on the support. Depending on the catalyst, a mixture of isomeric products is possible, as described in Shechter, L. and Wynstra, J., "Glycidyl Ether Reactions with Alcohols, Phenols, Carboxylic Acids, and Acid Anhydrides," Industrial and Eng. Chem (1956) 48:86–93.

Initially the following reaction is most likely as the second epoxy on the polyethylene oxide reacts with the reactive groups on the support:

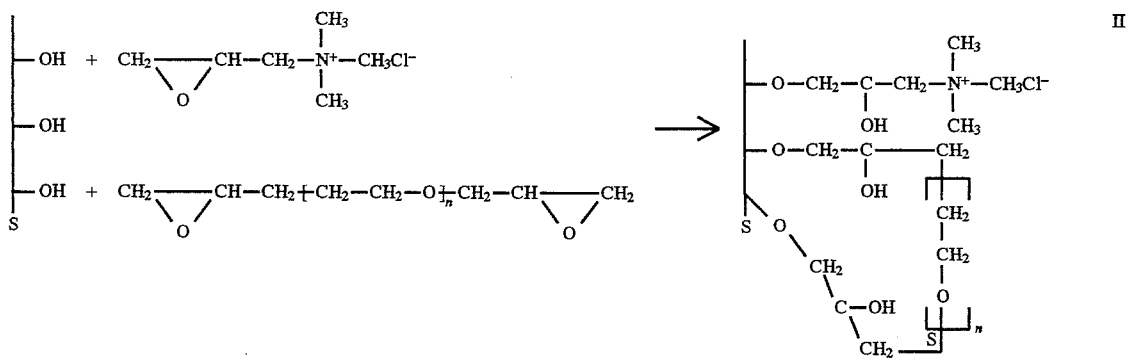

As the reaction proceeds, hydroxyl groups are generated which may in turn react with the epoxide in a "self-polymerization" reaction. One possible reaction combining a self-polymerization step with a surface reaction is illustrated by:

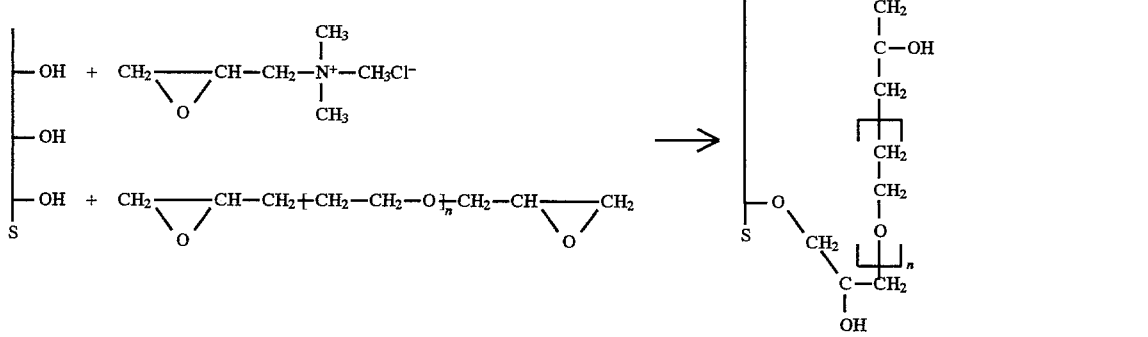

Further self-polymerization reactions will proceed as the hydroxyl groups generated from II and III are available for reaction with the epoxides on both the glycidyl trimethyl ammonium chloride and the bis glycidyl polyethylene oxide until steric limitations or epoxide unavailability occur.

The foregoing reactions are representative of reactions which occur between reactive epoxide groups on the quaternary amine and the polyethylene oxide and hydroxyl groups on the support. These reactions in the absence of catalysts usually require high temperatures and are easily catalyzed by acid, base, tertiary amines, or even self-catalyzed by the quaternary amine (Shechter, L., and Wynstra, J., "Glycidyl Ether Reactions with Alcohols, Phenols, Carboxylic Acids, and Acid Anhydrides," Industrial and Eng. Chem (1956) 48:86–93). Analogous reaction products occur using the range of starting materials described.

It is understood that the product of the reaction between the support and the quaternary amine and polyethylene oxide may include all the foregoing species.

When the support comprises reactive carboxyl groups, with epoxy groups on the quaternary amine and polyethylene oxide, the initial reaction proceeds as follows:

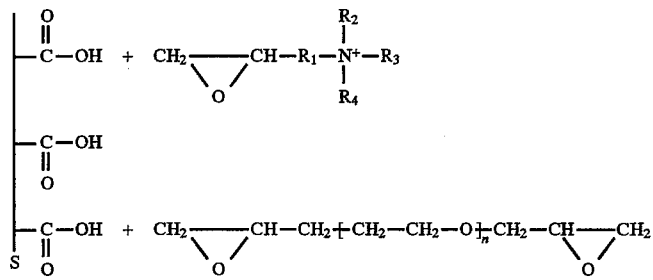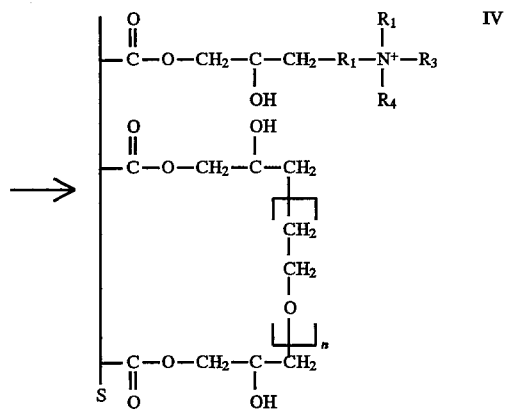

As previously discussed, this reaction and all subsequent reactions generate hydroxyl groups subject to further self-polymerization reactions.

When the support comprises reactive amine groups, with epoxy groups on the quaternary amine and polyethylene oxide, the initial reaction proceeds as follows:

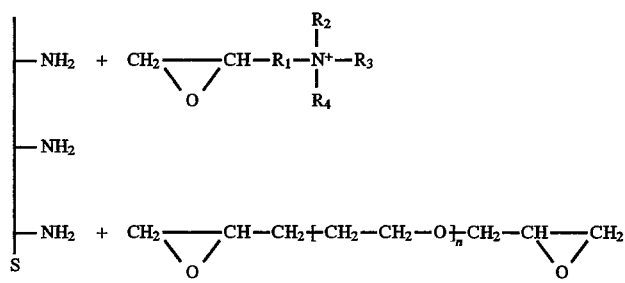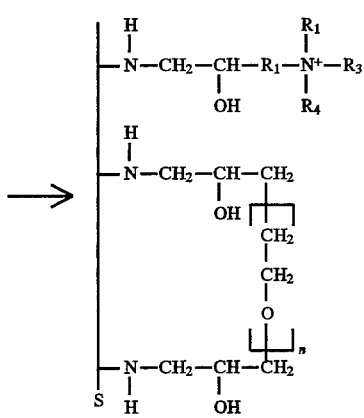

Again, this reaction and all subsequent reactions generate hydroxyl groups subject to further self-polymerization reactions.

The reactive groups on the support material could occur naturally, be reacted there, or be added during a coating process. Further, the support material may be comprised of any material including metal, polymers, cloth, etc. capable of being coated with a material comprising reactive groups, such as the polymeric materials discussed above naturally having, or modified to have, reactive groups. For example, hydroxyl-containing polymers such as ethylene vinyl alcohol can be used to coat polymers to provide reactive functionalities.

As will be readily appreciated by those skilled in the art, the support may use epoxy as the reactive group, and the quaternary amine and polyethylene oxide may use amine, carboxyl or hydroxy as the reactive groups. These support surfaces would not promote the aforementioned self-polymerizing reactions.

Hydroxy or other groups may be converted to epoxy groups on the support by reactions between hydroxy, carboxyl or amine groups on the support with a diepoxide as set forth below:

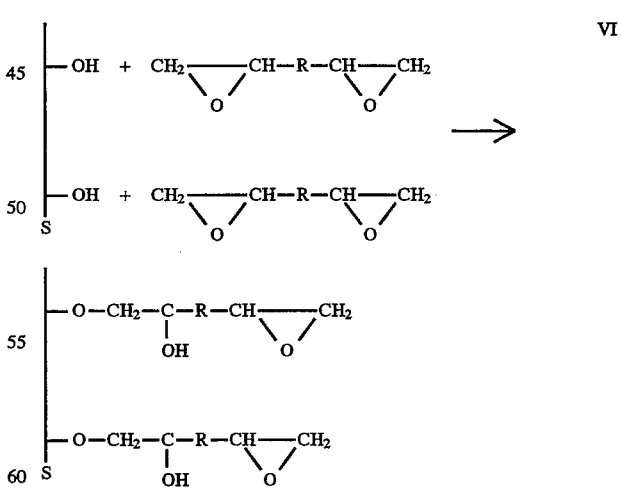

where R is as defined as $R_1$–$R_6$ above. These diepoxides may be added to the reaction mixture with the polyethylene oxide and quaternary amine so that the support materials claimed herein may be formed in a single-step method.

Similarly, supports containing amine or carboxyl reactive groups may be converted to supports containing epoxy reactive groups:

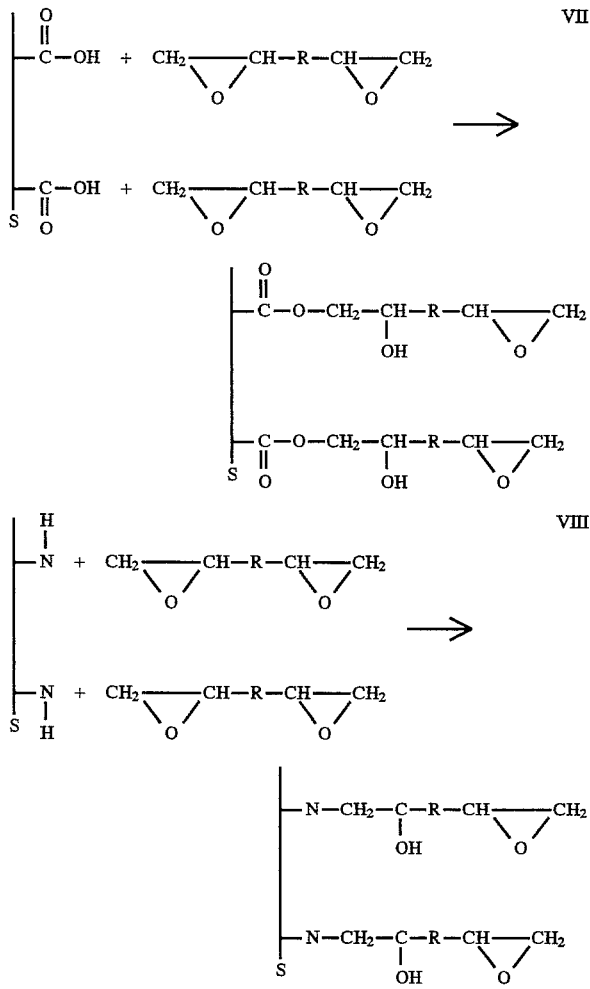

Examples of amine-terminated quaternary amines useful for reacting with supports having epoxy reactive groups are carbachol or choline chloride carbamate. Using carbachol and bis amine polyethylene oxide as examples, the reaction is as follows:

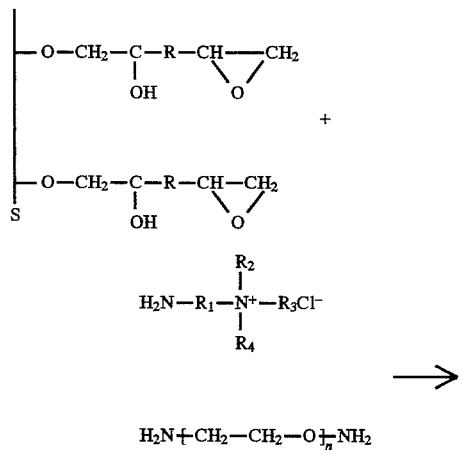

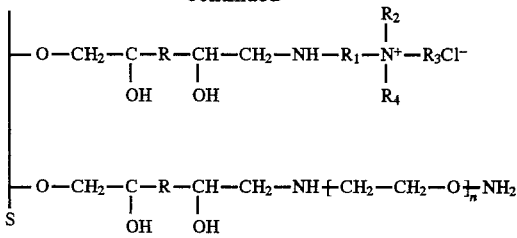

Supports presenting aldehyde groups may also be reacted with amine-terminated quaternary amines and polyethylene oxides.

Self-polymerization reactions involving the free end of the amine-terminated polyethylene oxide bond to the substrate may also occur as a result of the reaction of this amine group with the reactive group of the substrate.

As will be appreciated by those of skill in the art, reactions between the support and the quaternary amines and polyethylene oxides not utilizing epoxy groups as one of the reactive groups are also possible. For example, nylon supports having available amino and carbonyl groups may be converted to imidate salts of nylon, amine-substituted nylon, or aldehyde-substituted nylon which are then reacted under appropriate conditions with amine-substituted quaternary amines and amine-substituted polyethylene oxide utilizing the reactions taught in U.S. Pat. No. 4,800,016 incorporated herein by reference, and substituting amine-substituted quaternary amines and polyethylene oxides for the protamine taught in the patent to produce the compositions of this invention.

Also as taught in said U.S. Pat. No. 4,800,016, supports having reactive hydroxy groups such as cellulose can be reacted with cyanogen bromide to form imidocarbonate derivatives which may then be reacted with amines. Again, amine-substituted quaternary amines and polyethylene oxides may be substituted for protamine in the reactions taught in the patent. Further, as taught in said patent, polyurethanes may be treated with isocyanates to form isocyanate-terminated polyurethanes which may be reacted with amine-substituted quaternary amines and polyethylene oxides instead of the protamine taught in the patent, utilizing the reactions of said patent to form compositions of this invention.

The support can contain a mixture of reactive groups. Likewise, the quaternary amine and PEO can have different reactive groups. Supports of this invention may have two or more different quaternary amines having the same or different reactive groups.

As will be understood in the art, reaction conditions including pH and temperature are adjusted and optimized in accordance with the reactive species involved. See Shechter, L. and Wynstra, J. (1956), "Glycidyl Ether Reactions with Alcohols, Phenols, Carboxylic Acids and Acid Anhydrides," Industrial and Eng. Chem. 38:86–93 and Shechter, L., et al. (1956), "Glycidyl Ether Reactions with Amines," Industrial and Eng. Chem. 48:94–97.

Further included in the present invention is a method for selectively removing anionic species from solution by passing the solution in contact with the biocompatible anion exchange materials of the present invention. In a preferred embodiment, the anionic species is heparin and the solution is whole blood. A method for treating patients is also disclosed wherein a patient is treated with a medical agent (e.g., heparin) and later the medical agent is removed from the patient by extracorporeally passing a body fluid of the patient in contact with the biocompatible anion exchange material of the present invention. Methods for treating blood extracorporeally are also described wherein the extracorporeal process includes the introduction of heparin into the blood and, before reintroduction of the blood into the patient, passing the blood in contact with the biocompatible anion exchange material to remove the heparin.

The present invention includes the novel use of a known sheet material as a chromatographic support. The sheet material is comprised of a heat entangled blend of polyester (45%) and cellulose (55%) fibers. Also included is a method for the production of a biocompatible anion exchange material that is prepared by the treatment of such a hydroxylated chromatographic support material with a mixture of glycidyl trimethyl ammonium chloride (GTMAC) and bis glycidyl polyethylene oxide (GPEO) in order to react the hydroxyl groups on said support with the reagents to covalently bind quaternary ammonium units and long chain polymeric units on the surface of the support.

In this preferred embodiment of the invention wherein the carrier support is comprised of a sheet of heat-entangled blend of polyester (45%) and cellulose (55%) fibers, the nonwoven blend has a hydroentangled construction that is made without chemical binders or additions, has a basis weight of about 66 g/m$^2$, and a tensile strength of 15.9 kg in the machine direction and 9.1 kg in the cross direction. Such material can be obtained from The Texwipe Company (of Upper Saddle River, N.J.) as a clean room wiper sold under the trademark of "TECHNICLOTH". This sheet material has superior dry and wet strength relative to commercially available sheet support materials.

The TECHNICLOTH material has surface hydroxyl (—OH) groups that allow for the attachment of desired functional groups to the surface of the support. For example, the hydroxyl groups may be reacted with glycidyl groups, carboxylic acid or carboxylic acid derivatives. Alternatively, the surface hydroxyl groups may be derivitized prior to functionalization. In one embodiment, the hydroxyl groups are oxidized to aldehydes according to procedures well known in the art, and the aldehydes are reacted with the primary amines of proteins to form covalently bound protein chromatographic materials. The hydroxyl groups on the surface of the TECHNICLOTH are like those found in most carrier support materials, and the vast body of knowledge for derivitizing supports would be well known to those skilled in the art.

In a preferred embodiment of this invention, anion exchange materials are prepared by reacting carrier support materials simultaneously with a plurality of chemical species that will react with the hydroxyl groups of the support. A first chemical species will incorporate ion exchange capability on the surface of the support, and a second chemical species will convey biocompatibility to the support. In a preferred embodiment, the ion exchange capability is created by the use of quaternary ammonium groups and the preferred first chemical species is glycidyl trimethyl ammonium chloride (GTMAC). In a preferred embodiment, the biocompatibility is created by using polyethylene oxide units, and the preferred second chemical is bis glycidyl polyethylene oxide (GPEO).

It is to be understood that other chemicals could be used to effect the same or substantially similar results, and that such chemicals would be known or readily apparent to those of ordinary skill in the art. The only requirement is that the selected chemicals be capable of reacting with the reactive sites of the chosen support material.

In a preferred embodiment, the given support material is immersed in an aqueous solution containing from 5 to 60 weight percent GTMAC and 0.1 to 10 weight percent GPEO for from 0.5 to 24 hours. In a preferred embodiment, the GTMAC utilized is a 70% aqueous solution, and the GPEO is a solid material dissolved in aqueous solution. The reaction may be catalyzed by the addition of a base such as NaOH. GPEO to be used in this invention contains greater than 10 and less than 200 repeating ethylene oxide units. In a preferred embodiment, the GPEO contains greater than 25 and less than 100 repeating units, and in a more preferred embodiment, the GPEO contains about 70–80 repeating units and has a molecular weight of about 3,300.

The weight ratio of GTMAC to GPEO in the solution used to create the anion exchange materials of the present invention is between about 50 to about 600, more preferably between about 50 and 200. In the preferred embodiment, the weight ratio of GTMAC to GPEO is about 80. The solution comprises between about 5 and about 60 weight percent of the quaternary amine and between about 0.1 and about 10 weight percent of polyethylene oxide. It can be roughly assumed that the surface of the anion exchange material contains a ratio of ammonium salt units to polyethylene oxide units roughly equivalent to the ratio used in the solution.

In the preferred embodiment, bis glycidyl polyethylene oxide is used, and it may be assumed that in at least some initial reactions both glycidyl functionalities will react with the surface of the support and with reactive species formed on the added quaternary amine or polyethylene oxide moieties via self-polymerization reactions as described above to form "looped" species. It is believed, however, that monoreactive polyethylene oxide units that cannot form such species would be equally effective in conveying biocompatibility to the surface of the support.

In one embodiment of the present invention, the anion exchange materials are utilized to remove anionic species from bodily fluids. Particularly useful is the removal of anionic species from whole blood. Such species include heparin, bilirubin, barbiturates, and any other anionic species (either endogenous or exogenous) that may be found naturally in the blood or that has been introduced into the blood either as part of a medical treatment or as a mood altering drug. In the preferred embodiment, the bodily fluid is passed, extracorporeally, in contact with the anion exchange material. However, the present invention also includes the use of anion exchange material in a device such that bodily fluids are passed in contact with the material intracorporeally.

The removal of anionic species from bodily fluids may be part of a medical treatment as described in co-pending U.S. patent application Ser. No. 07/562,009, specifically incorporated herein by this reference. According to this method, a medical agent is administered to a patient and following a given period of time, the agent is removed from the patient's system by extracorporeally passing a body fluid of the patient in contact with the anion exchange material to specifically remove the agent. In one embodiment of this method, the medical agent is heparin (administered to prevent blood clotting during certain surgical procedures) and the extracorporeal treatment occurs following surgery.

In a variant embodiment of this method, both the treatment of the bodily fluid with an anionic medical agent and the removal of the agent with the anionic exchange material are extracorporeal. For example, blood may be removed from a patient for dialysis or plasma exchange, and it may be desirable to add heparin to the blood before it enters the processing equipment, and remove it from the blood before it reenters the patient.

The present invention also includes the use of heparin introduction and removable modules associated with extracorporeal blood processing equipment. The heparin introduction module may consist of any automated or manual fluid metering devices such as are familiar to those skilled in the art. The heparin removal modules would consist of means for passing the processed blood in contact with the anion exchange materials of the present invention. Means for passing fluids in contact with sheet ion exchange materials are also well known in the prior art. Blood processing includes plasma exchange, dialysis, and oxygenation, and the use of other well known blood processing equipment where it is advantageous to add heparin to the blood prior to processing.

Although in the preferred embodiment the anion exchange materials of this invention are utilized in the removal of anionic material from whole blood, the anion exchange materials may also be used to remove such material from other bodily fluids, e.g., plasma and peritoneal fluids, as well as from aqueous or organic based solvent streams.

The above descriptions of this invention can be better understood when read in conjunction with the Examples presented below. It should be understood, however, that the present invention must not be limited to the specifics of such Examples.

EXAMPLES

Example 1

Cellulosic material

In the following example, the disclosed process is used to make an anionic exchange material from a flat sheet of TECHNICLOTH. The utility of the material is then demonstrated with the in vitro removal of heparin from bovine blood. Heparin removal with the TECHNICLOTH reacted with GTMAC and GPEO (hereinafter referred to as TECH-GG) is compared with protamine sulfate also immobilized on TECHNICLOTH using the procedure recommended by Yang (U.S. Pat. No. 4,800,016) and with the anion exchange paper available from Cuno, Inc. (Cuno QAE). The biocompatibility is evaluated from the amount of platelets removed from bovine blood with each of these materials. The following describes the materials used, the reaction of GTMAC and GPEO with the TECHNICLOTH, the heparin removal experimental protocol, and the results.

The glycidyl trimethyl ammonium chloride (GTMAC) is obtained from the Degussa Corporation of Ridgefield Park, N.J. as QUAB-151, a 70% aqueous solution. The bis glycidyl polyethylene oxide is obtained in solid form (Cat. #P2672, polyoxyethylene, bis glycidyl) from Sigma Chemical in St. Louis, Mo. Sodium hydroxide (NaOH) is used to catalyze the reaction and is obtained from Curtin Matheson Scientific (CMS) in Aurora, Colo. Sodium chloride (NaCl), dibasic sodium phosphate, and monobasic sodium phosphate are used to prepare buffers and are also obtained from CMS. The bovine blood is collected from donor cows the morning of use, and is provided by Hemo Lab of Broomfield, Colo. Beef lung heparin is obtained from Organon Inc. of West Orange, N.J., in 1000 USP units/ml ampules.

Five, 5×20 cm sheets of TECHNICLOTH are immersed in a 0.3M NaOH aqueous solution containing 40 g % GTMAC and 0.5 g % GPEO for 24 hours. This is done by first dissolving 5 gms of GPEO and 12.95 gms of NaOH in 360 ml water in a 1100 ml jar. The TECHNICLOTH sheets are then added and the contents swirled. Immediately, 610 gms of liquid QUAB-151 (GTMAC) are added, followed by water to a total volume of 1080 mls. The contents are mixed and the jar is let set for 24 hours with no further agitation.

At the end of the 24 hours the substrate sheets are removed and washed with copious amounts of water, then rinsed with six 1000 ml batches of equilibration buffer (0.1M sodium phosphate, 0.5M NaCl, pH 8.0) and left at 4° C. overnight in the same. The equilibration buffer is then replaced with PBS (phosphate buffered saline: 0.01M sodium phosphate, 0.85 g % NaCl, Pb 7.4) and the substrate sheets stored at room temperature until their use in the heparin removal experiments.

A test heparin removal filter (HRF) is constructed by sandwiching one 5×20 cm sheet of a candidate material between two sheets of polypropylene netting. The three sheets are then placed in a fixed channel device through which blood can be pumped. This device, constructed of polycarbonate, holds the filter material in place so that blood can be passed with equal velocity on both sides. The depth of the 5 cm wide flow path can be varied by the use of stainless steel shims. By using a thicker shim for a thicker candidate material, the depth of the flow path can be held constant. The purpose of the netting is to separate the filter material from the housing wall to create equal flow paths. Blood enters the bottom of the housing, is split by the filter material, and flows vertically (along the 20 cm dimension).

For the TECHNICLOTH-protamine sulfate reaction, the procedure of Yang is followed with activation by cyanogen bromide at a concentration of 0.1 g/ml and exposure time of 5 minutes. In the immobilization step, the protamine concentration is 10 mg/ml with overnight exposure. The Cuno material is used as recommended by Cuno Inc.

In order to test the heparin removal efficiency and blood cell compatibility of the TECH-GG and demonstrate the disclosed process, an experimental protocol was designed to simulate the envisioned use of a heparin filter. A reservoir of bovine blood containing 8 units/ml of beef lung heparin is circulated through the fixed channel device. The reservoir volume is chosen so that the total system volume (prime of the housing with PBS includes) is 225 mls. The reservoir is pumped at 150 ml/min and blood samples are taken at timed intervals. The blood samples are analyzed for heparin by the Azure A method (U.S. Pat. No. 4,678,660 of McGary, incorporated by reference herein), and eleven hematological parameters are evaluated with a Coulter Counter Model S-Plus IV, of which the most sensitive indicator of blood trauma is the platelet count. After the total volume of 225 mls has been circulated through the filter 10 times (15 minutes), the experiment is terminated. Multiple passes through the filter insure that "activated" platelets will be removed.

The heparin removal efficiency of the TECH-GG is compared to the Cuno-QAE material and immobilized protamine, and the results are shown in FIG. 1. The "fraction of heparin remaining," or the amount of heparin remaining in the reservoir over the initial amount (corrected for dilution) is plotted versus the number of reservoir recirculations (225 ml) for each of these materials in FIG. 1.

Figure 2:
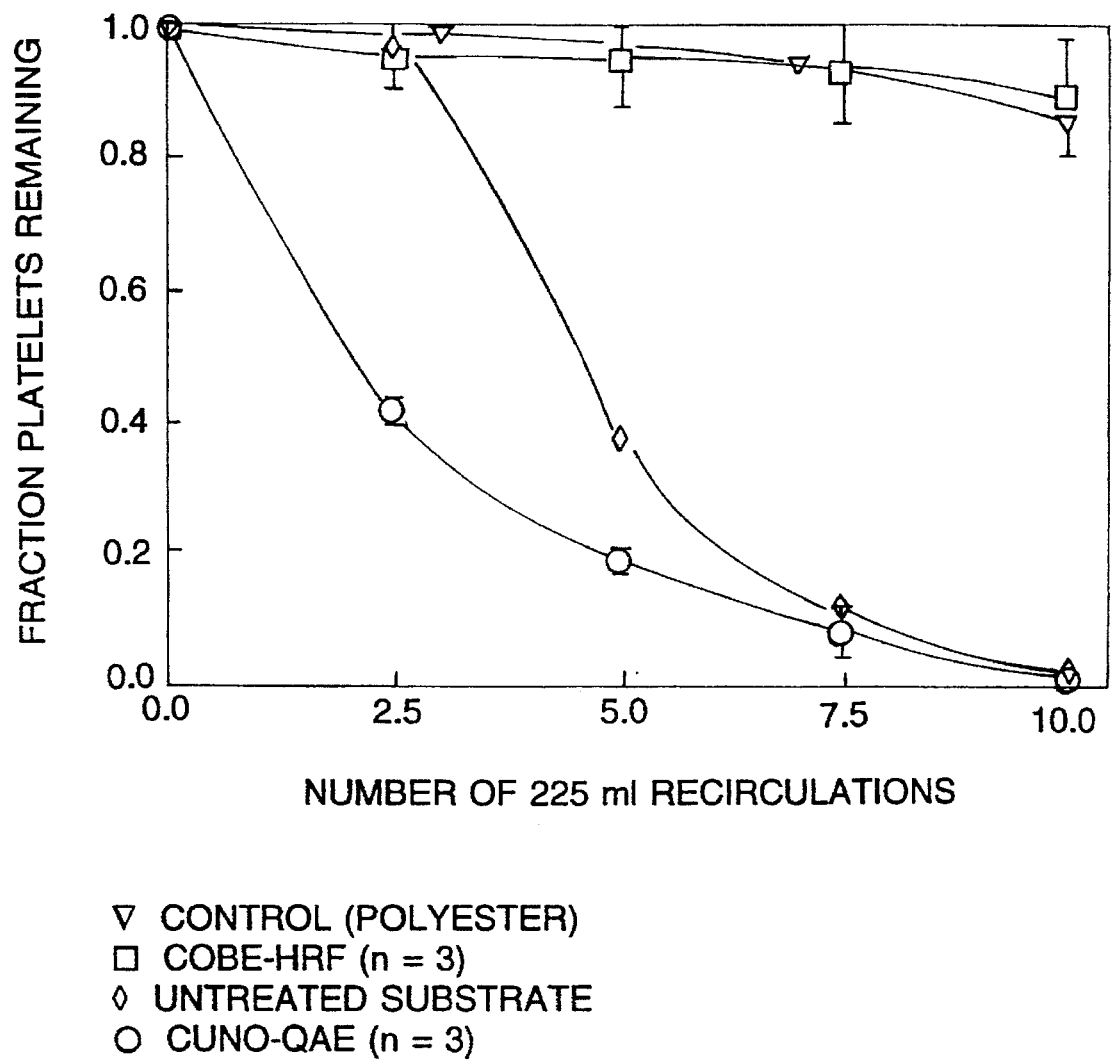
FIG. 2 is a graph showing the in vitro platelet removal from bovine blood. The graph plots the fraction of platelets remaining in the blood sample versus the number of times the total volume of blood was circulated in contact with a given chromatographic material. Results are shown for a polyester control (▽), a biocompatible anion exchange material of the present invention (□), a chromatographic support material of the present invention (◇), and a commercially available anion exchange material known as Cuno QAE (○).

In FIG. 2, the same experimental protocol described above is used to determine the amount of platelets removed from the bovine blood following repeated passes through the sample containing reservoir.

The results of FIGS. 1 and 2 show that the anion exchange materials of the present invention are effective in heparin removal, while retaining excellent biocompatibility, as evidenced by their not significantly depleting the blood of platelets.

Example 2

Agarose Beads

Agarose beads, Sepharose™ are purchased from Pharmacia, Uppsala, Sweden. Forty (40) g of glycidyl trimethyl ammonium chloride and 5 g of glycidyl polyethylene oxide having a molecular weight of 3350 are solubilized in 100 ml of deionized water containing 3 g NaOH. Fifty (50) ml of said agarose beads are soaked in said solution for a period of 1 to 24 hours.

Then 225 ml blood containing 5–15 units/ml heparin is assayed for platelet content as described in Example 1, then recirculated at 50–150 ml/min over a bed of said agarose beads comprising trimethyl ammonium chloride and polyethylene oxide groups for a period of 5–60 minutes. The processed blood is then assayed as described in Example 1 for heparin and platelet content. The results indicate removal of more than 90 percent heparin and less than 20% of the original platelets.

Example 3

Polyurethane

A 100 cm² (5×20 cm) Pellathane™ polyurethane sheet having reactive amine groups (available from Upjohn), is soaked in toluene for approximately ten minutes to remove surface impurities. After soaking, the support material is placed in 50 ml of 0.25M methylenebis (4-phenylisocyante) in trimenthylpentane under dry nitrogen, and incubated at approximately 80 degrees C for one hour with gentle agitation. For immobilization of the quaternary amine and polyethylene oxide, the activated support material is washed with ethanol and distilled water and placed in a 100 ml solution containing 40 g 2-aminoethyl trimethyl ammonium chloride from Aldrich Chemical, Milwaukee, Wis. and 5 g bis amine polyethylene oxide from Sigma Chemical, St. Louis, Mo., having a molecular weight of 3350 in physiological saline buffer, pH 7.4, for a period of 1–24 hours. A test heparin removal filter is constructed by sandwiching one sheet of the treated polyurethene between two sheets of polypropylene netting in a fixed channel device through which blood can be pumped.

The construct is tested for heparin and platelet removal as described in Example 1, with results as described in Example 2.

Example 4

Nylon

A 5×20 cm sheet of nylon fabric from Pomona Textiles, Pomona, Calif., is placed in 100 ml of triethyloxonium tetrafluroborate solution (10% w/v in dry dichloromethane) and incubated at room temperature for approximately 15 minutes. The sheet is then washed through for approximately two minutes with dichloromethane and for two minutes with dioxane. Immediately after the dioxane wash, the sheet is placed in 100 ml of 1,6-diaminohexane solution (10% w/v in methanol), incubated at room temperature for approximately three hours, and then treated with 5% (w/v) glutaraldehyde in 0.2M borate buffer (pH 8.5) for approximately 20 minutes at room temperature. For immobilization of the quaternary amine and polyethylene oxide, the sheet is washed with ethanol and distilled water and placed in a 100 ml solution containing 40 g 2-aminoethyl trimethyl ammonium chloride from Aldrich Chemical, Milwaukee, Wis., and 5 g bisamine polyethylene oxide from Sigma Chemical, St. Louis, Mo., having a molecular weight of 3350 in 0.1M phosphate buffer having a pH of 8.0 and containing 0.5M NaCl.

The construct is tested for heparin and platelet removal as described in Example 1, with results as described in Example 2.

Example 5

Epoxy-Activated Cellulose with Hydroxy on Reactants

Fifteen (15) g of epoxy-activated cross-lined agarose purchased from Sigma Chemical, St. Louis, Mo., is washed and reswelled with deionized and distilled water (100 ml/g). The swollen beads are placed in a 100 ml solution containing 40 g of choline chloride (also from Sigma) and 10 g of bisamine polyethylene oxide (MW 500) from Sigma Chemical, and 3 g NaOH, and gently stirred for a period of 1–24 hours. Excess reactants are then washed away with copious amounts of water followed by bicarbonate buffer (0.1M, pH 8.0), then acetate buffer (0.1M, pH 4), and saline at physiological pH.

The beads are tested for heparin and platelet removal as described in Example 2, with similar results.

Example 6

Zetaffinity™ Aldehyde-Containing Support with Amine on Reactants

A 50×20 cm sheet of preactivated amino Zetaffinity™ from Cuno, Inc. of Meriden, Conn., is placed in a 100 ml solution of 0.1M sodium phosphate buffer pH 7.6 containing 40 g of Girard's reagent (carboxymethyl trimethylammonium chloride hydrazide) from Aldrich Chemical and 5 g of bis amine polyethylene oxide from Sigma Chemical (MW3350) for 1 to 24 hours. Excess reactants are removed by rinsing with more than 1000 mls of the 0.1M sodium phosphate buffer. The sheet is then rinsed with more than 1000 ml of 0.1M borate buffer and then with more than 1000 mls of a blocking buffer containing glycine ethylester hydrochloride (2%) in the 0.1M borate buffer with the pH adjusted to 8.2, followed by three additional 100 ml washes with NaBH$_4$ (sodium borohydrate) at 100 mg per 100 ml 0.1M borate buffer to reduce the Schiff base reaction to a more stable linkage. A final wash with more than 1000 mls of physiological buffer is required.

The construct is tested for heparin and platelet removal as described in Example 3 with similar results.

Example 7

Zetaffinity™ Support with Reactive Hydroxyl Groups and Hydroxyl on Reactants A 5×20 cm sheet of hydroxy Zetaffinity™ from Cuno, Inc., Meriden, Conn., is placed in 100 ml of 1M NaOH containing 2 mg/ml NaBH$_4$. Twenty (20) g butanedioldiglycidyl ether is added and left stand for 5 to 10 hours. The sheet is then rinsed with copious amounts of water and placed in 100 ml of aqueous solution containing 40 g of choline chloride from Sigma Chemical and 10 g polyethylene oxide (MW 3350) and 3 g NaOH with gentle stirring for 1–24 hours. Excess reactants are washed away with copious amounts of water followed by saline at pH 7.4.

The construct is tested for heparin and platelet removal as described in Example 3 with similar results.

We claim:

1. A biocompatible anion exchange material, for removal of heparin from a fluid also containing platelets, made from components comprising:
   a. a polymeric support having a first reactive group and a second reactive group spaced apart so as to allow for ionic binding of heparin to said anion exchange material without removal of platelets;
   b. a quaternary amine moiety covalently bonded to said first reactive group;
   c. a polyethylene oxide moiety having between about 10 and about 200 repeating units covalently bonded to said second reactive group;
   wherein said quaternary amine and said polyethylene oxide moieties are substantially homogeneously distributed on said support at a molar ratio of charged amine moiety to ethylene oxide repeating unit of between about 0.3:1 and about 450:1.

2. The anion exchange material of claim 1 wherein said molar ratio of quaternary amine moiety to polyethylene oxide moiety is about 30.

3. The anion exchange material of claim 1 wherein said polyethylene oxide moiety has at least about 25 repeating units.

4. The anion exchange material of claim 1 wherein said polyethylene oxide moiety has between about 70 and about 80 repeating units.

5. The anion exchange material of claim 1 wherein said quaternary amine moiety is hydroxy butyl ether-trimethyl ammonium.

6. The anion exchange material of claim 1 wherein said quaternary amine moiety comprises a polyethylene oxide moiety covalently bonded thereto.

7. The anion exchange material of claim 6 wherein said polyethylene oxide moiety covalently bonded to said quaternary amine moiety is also covalently bonded to said support.

8. The anion exchange material of claim 1 wherein said polyethylene oxide moiety is bonded to said support at two sites.

9. The anion exchange material of claim 1 wherein said support comprises a material selected from the group consisting of polysaccharides, agarose, cellulose, polyurethane, nylon, polyvinyl alcohol, polystyrene, polyacrylamide, and polyolefins presenting reactive groups, and combinations thereof.

10. A process for preparing an anion exchange material comprising:
   a. providing a support material comprising reactive groups capable of serving as covalent bonding sites;
   b. contacting said support material with a quaternary amine and a polyethylene oxide having between about 10 and about 200 repeating units, said quaternary amine and said polyethylene oxide each having reactive groups capable of reacting at different sites with said reactive groups of said support material to form covalent bonds, whereby said quaternary amine and said polyethylene oxide are covalently bonded to said support material.

11. The process of claim 10 wherein said polyethylene oxide and said quaternary amine are solubilized in a solution, and said support material is contacted with said solution.

12. The process of claim 11 wherein said solution comprises between about 5 and about 60 weight percent of said quaternary amine and between about 0.1 and about 10 weight percent of said polyethylene oxide.

13. The process of claim 11 wherein said support material is contacted with said solution for a period of between about 0.5 and about 24 hours.

14. The process of claim 10 wherein the molar ratio of quaternary amine to polyethylene oxide is about 30.

15. The process of claim 10 wherein said polyethylene oxide has at least about 25 repeating units.

16. The process of claim 10 wherein said polyethylene oxide has between about 70 and about 80 repeating units.

17. The process of claim 10 wherein said reactive groups of said support material are selected from the group consisting of epoxy, aldehyde, hydroxyl, carboxyl, amine, and combinations thereof.

18. The process of claim 10 wherein said reactive groups of said quaternary amine and said polyethylene oxide are independently selected from the group consisting of epoxy, aldehyde, hydroxyl, carboxyl, amine, and combinations thereof.

19. The process of claim 10 wherein said support material comprises epoxy or aldehyde moieties capable of reacting with said quaternary amine and said polyethylene oxide to form covalent bonds.

20. The process of claim 10 wherein said quaternary amine and said polyethylene oxide comprise epoxy, or aldehyde moieties capable of reacting with said support material to form covalent bonds.

21. The process of claim 10 wherein said support material comprises a material selected from the group consisting of polysaccharides, agarose, cellulose, polyurethane, nylon, polyvinyl alcohol, polystyrene, polyacrylamide, and polyolefins presenting reactive groups, and combinations thereof.

22. The process of claim 10 wherein said support material comprises cellulose.

23. The process of claim 10 wherein said quaternary amine is glycidyl trimethyl ammonium chloride.

24. The process of claim 10 wherein said polyethylene oxide is bis glycidyl polyethylene oxide.

25. A biocompatible anion exchange material made by the method of claim 10.

26. A biocompatible anion exchange material made by the method of claim 11.

27. A biocompatible anion exchange material made by the method of claim 12.

28. A biocompatible anion exchange material made by the method of claim 21.

29. A biocompatible anion exchange material, for removal of heparin from a fluid also containing platelets, made from components comprising:
   a. a polymeric support having first reactive groups and second reactive groups spaced apart so as to allow for ionic binding of heparin to said anion exchange material, without removal of platelets, said support being a polymer which contains or has been coated or reacted to provide reactive groups selected from the group consisting of hydroxyl, amino, carboxyl, aldehyde, or epoxy reactive groups, or mixtures of the foregoing;
   b. quaternary amine moieties covalently bonded to said first reactive groups;
   c. polyethylene oxide moieties having between about 10 and about 200 repeating units covalently bonded to said second reactive groups;
   d. said quaternary amine moieties and said polyethylene oxide moieties being spaced apart so as to allow ionic binding of heparin to said anion exchange material without binding of platelets;

wherein said quaternary amine and said polyethylene oxide moieties are substantially homogeneously distributed on said support at a molar ratio of charged amine moiety to ethylene oxide repeating unit of between about 0.3:1 and about 450:1.

30. A biocompatible anion exchange material according to claim 1, wherein said first reactive group and said second reactive group are the same chemical functional group.

31. A biocompatible anion exchange material according to claim 1, wherein said first reactive group and said second reactive group are different chemical functional groups.

32. A biocompatible anion exchange material according to claim 29, wherein said first reactive group and said second reactive group are the same chemical functional group.

33. A biocompatible anion exchange material according to claim 29, wherein said first reactive group and said second reactive group are different chemical functional groups.

* * * * *

UNITED STATES PATENT AND TRADEMARK OFFICE
CERTIFICATE OF CORRECTION

PATENT NO. : 5,648,070
DATED : July 15, 1997
INVENTOR(S) : Ben F. Brian, III, et al.

It is certified that error appears in the above-indentified patent and that said Letters Patent is hereby corrected as shown below:

On the title page, item [56]:

<u>In the References Cited</u>
The third reference on page 2 please delete "Hou, L.C." and replace with --Hou, K.C.--.

<u>In the Specification</u>
Column 1, Line 34, please delete "Z4:436-442" and replace with --14:436-442--.

Column 3, Line 7, please delete "ammoniumchloride" and replace with --ammonium chloride--.

Column 12, Equation IV, please delete "$R_1$" and replace with --$R_2$-- as shown below:

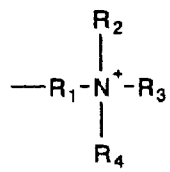

Column 12, Equation V, please delete "$R_1$" and replace with --$R_2$-- as shown below:

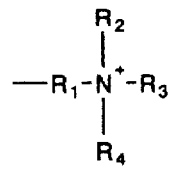

UNITED STATES PATENT AND TRADEMARK OFFICE
CERTIFICATE OF CORRECTION

PATENT NO. : 5,648,070
DATED : July 15, 1997
INVENTOR(S) : Ben F. Brian, III, et al.

It is certified that error appears in the above-indentified patent and that said Letters Patent is hereby corrected as shown below:

Column 18, line 11, please delete "Pb 7.4" and replace with --Ph 7.4--.

Column 20, line 37, please delete "(MW3350)" and replace with --(MW 3350)--.

Signed and Sealed this

Seventh Day of October, 1997

*Attest:*

BRUCE LEHMAN

*Attesting Officer*   Commissioner of Patents and Trademarks